(12) United States Patent
Fenster et al.

(10) Patent No.: US 6,342,891 B1
(45) Date of Patent: Jan. 29, 2002

(54) SYSTEM AND METHOD FOR THE DYNAMIC DISPLAY OF THREE-DIMENSIONAL IMAGE DATA

(75) Inventors: Aaron Fenster; Kenneth Dunne, both of London (CA)

(73) Assignee: Life Imaging Systems Inc. (CA)

( * ) Notice: Subject to any disclaimer, the term of this patent is extended or adjusted under 35 U.S.C. 154(b) by 0 days.

(21) Appl. No.: 09/230,558
(22) PCT Filed: Jun. 25, 1998
(86) PCT No.: PCT/CA98/00625
   § 371 Date: Dec. 17, 1999
   § 102(e) Date: Dec. 17, 1999
(87) PCT Pub. No.: WO99/00675
   PCT Pub. Date: Jan. 7, 1999

Related U.S. Application Data
(60) Provisional application No. 60/050,779, filed on May 25, 1997.

(51) Int. Cl.⁷ .............................................. G06F 15/00
(52) U.S. Cl. ...................................................... 345/473
(58) Field of Search ................................. 345/473, 474, 345/475; 382/44

(56) References Cited

U.S. PATENT DOCUMENTS

| | | | | |
|---|---|---|---|---|
| 4,791,567 A | * | 12/1988 | Cline et al. ............ | 364/413.13 |
| 5,315,512 A | * | 5/1994 | Roth ..................... | 364/413.25 |
| 5,396,890 A | * | 3/1995 | Weng .................... | 128/660.07 |
| 5,454,371 A | | 10/1995 | Fenster et al. .............. | 128/660 |
| 5,562,095 A | | 10/1996 | Downey et al. ............ | 128/660 |
| 5,842,473 A | | 12/1998 | Fenster et al. ......... | 128/660.09 |

FOREIGN PATENT DOCUMENTS

WO     WO / 97 20288    *   6/1997

* cited by examiner

*Primary Examiner*—Phu K. Nguyen
(74) *Attorney, Agent, or Firm*—Katten Muchin Zavis

(57) ABSTRACT

The present invention provides a system for the dynamic display of three-dimensional (3D) images of a target, comprising: memory means to store the plurality of time-dependent 3D image data sets; an address pointer defining an independent address of a location in the memory means of each time-dependent 3D image data set; and display means utilizing the address pointer successively to retrieve a time-dependent 3D image data set from memory and display a time-dependent 3D image corresponding to the time-dependent 3D image data set for a selected period of time. A method for dynamic display of 3D images is also provided.

4 Claims, 3 Drawing Sheets

SYSTEM AND METHOD FOR THE DYNAMIC DISPLAY OF THREE-DIMENSIONAL IMAGE DATA

This application claims the benefit of provisional application No. 60/050,779, filed Jun. 25, 1999.

TECHNICAL FIELD

The present invention relates to the field of image data display. More specifically, the present invention relates to a system and method for the dynamic display of three-dimensional image data.

BACKGROUND ART

Three-dimensional (3D) ultrasound imaging is a technique in which a set of spatially related two dimensional ultrasound slices (tomograms) of a target are collected and mathematically converted to create a virtual Cartesian ultrasound volume. This virtual ultrasound volume facilitates the visualization of non-acquired slices of the target and a variety of rendered surfaces and projections of the target otherwise unobtainable using two-dimensional (2D) ultrasound imaging.

High fidelity 3D ultrasound requires, by definition, a data set in which the spacial relationship between the individual ultrasound slices is precisely known. High fidelity ultrasound is important for the accurate assessment of volumes and the appreciation of target geometry. The conventional method of choice for obtaining the precise spatial relationship between ultrasound slices is to actively constrain the position of each ultrasound slice. This is achieved by controlling the position of the ultrasound probe during generation of the slices by use of a motorized positioning device (mechanical scanning). Examples of 3D ultrasound imaging systems are described in detail in U.S. Pat. No. 5,454,371 (Fenster et al.) and U.S. Pat. No. 5,562,095 (Downey et al.), the contents of each of which are hereby incorporated by reference.

In the three-dimensional ultrasound imaging systems described in the afore-mentioned United States patents, when a succession of two-dimensional images have been captured and digitized, the two-dimensional images are stored as a stack to form an image data array. Before a three-dimensional image of the scanned volume can be created and viewed by a user, the image data array must be reconstructed to form a volumetric image array. This type of reconstruction, in which every pixel in every two-dimensional image slice is converted into an appropriate voxel in an image volume (i.e. volumetric image array) prior to display is known as "full volume" reconstruction. The generation of the complete volume array is somewhat inefficient, i.e. it is a time-consuming intermediate stage. Full volume reconstruction and display of a three-dimensional image using a conventional hardware platform can take upward of one minute and, therefore, has limited application in situations where immediate display of an acquired image is desirable.

In an attempt to overcome the drawbacks associated with full volume reconstruction, the applicants developed a so-called "fast" reconstruction process which is described in copending U.S. patent application Ser. No. 08/562,590 (which corresponds to International patent application publication number WO 97/20288), and U.S. provisional patent application serial No. 60/041,345, filed Mar. 21, 1997, the contents of each of which are hereby incorporated by reference.

In fast reconstruction, only the specific image data from the two-dimensional image slices that are actually required to view the user-selected image undergoes reconstruction. In other words, only the image data necessary to view the surface of user-selected image (i.e. as opposed to all of the data representing the entire volume of the target) is used for reconstruction. If, for example, the users wishes to view a particular image of the target volume, the computer uses associated calibration and acquisition parameters of the collected two-dimensional image slices to determine special "look-up" tables which speed up the determination of which data points from the two-dimensional image slices are required to be displayed on the monitor. Only the two-dimensional data points necessary to produce the desired image are reconstructed. There is no necessity to construct a full volume image array. Accordingly, this fast reconstruction is more efficient than conventional full volume reconstruction, i.e. it is less time-consuming (less than ½ second).

Both "full volume" and "fast" reconstruction techniques are capable of generating and displaying high quality, single, three-dimensional images of a target, i.e., a temporal "snap-shot" of the target. These techniques are particularly useful in displaying images of non-dynamic, effectively stationary targets such as the breast, prostate or liver. However, the display of a single "snap-shot" is not optimally effective for imaging a dynamic target such as the heart or lungs.

DISCLOSURE OF THE INVENTION

It is an object of the present invention to provide a system and method for dynamic image display which obviates and mitigates at least one of the disadvantages of the prior art.

Accordingly, in one aspect the present invention provides a system for the dynamic display of three-dimensional (3D) images of a target, comprising:
  memory means to store a plurality of time-dependent 3D image data sets;
  an address pointer defining an independent address of a location in the memory means of each time-dependent 3D image data set; and
  display means utilizing the address pointer successively to retrieve a time-dependent 3D image data set from memory and display a time-dependent 3D image corresponding to the time-dependent 3D image data set for a selected period of time.

In another of its aspects, the present invention provides a system for the dynamic display of three-dimensional (3D) images of a target volume, the system comprising:
  scanning means to scan a target volume and generate a succession of digitized two-dimensional (2D) images thereof;
  timing means to determine the time interval between generation of the succession of 2D images;
  reconstruction means to generate a plurality of time-dependent 3D image data sets of the target volume from the succession of digitized 2D image;
  memory means to store the plurality of time-dependent 3D image data sets;
  an address pointer defining an independent address of a location in the memory means of each time-dependent 3D image data set; and
  display means utilizing the address pointer successively to retrieve a time-dependent 3D image data set from memory and display a time-dependent 3D image corresponding to the time-dependent 3D image data set for a selected period of time.

In yet another of its aspects, the present invention provides a method for the dynamic display of three-dimensional (3D) images of a target, comprising the steps:

(i) storing a plurality of time-dependent 3D image data sets in a memory;

(ii) defining an independent address of a location in the memory means for each time-dependent 3D image data set; and (iii) retrieving a time-dependent 3D image data set from memory;

(iv) displaying the time-dependent 3D image corresponding to the time-dependent 3D image data set for a selected period of time; and (v) repeating Steps (iii) and (iv) for each remaining time-dependent 3D image data set.

In yet another of its aspects, the present invention provides a method for the dynamic display of three-dimensional (3D) images of a target volume, the system comprising:

(i) scanning a target volume and generating a succession of digitized two-dimensional (2D) images thereof;

(ii) determining the time interval between generation of the succession of 2D images;

(ii) generating a plurality of time-dependent 3D image data sets of the target volume from the succession of digitized 2D image;

(iii) storing a plurality of time-dependent 3D image data sets in a memory;

(iv) defining an independent address of a location in the memory means for each time-dependent 3D image data set; and (v) retrieving a time-dependent 3D image data set from memory;

(vi) displaying the time-dependent 3D image corresponding to the time-dependent 3D image data set for a selected period of time; and (vii) repeating Steps (v) and (vi) for each remaining time-dependent 3D image data set.

The terms "dynamic image display" and "dynamic display of three-dimensional images" are used interchangeably throughout this specification and are intended to include any method and/or system capable of displaying, in a time-dependent sequential manner, a three dimensional image of a target (e.g., organ, bodily structure, etc.) which is in a state of motion. The effect of this is to enable three dimensional visualization of changes in a target over time. Non-limiting examples of applications of dynamic image display in which the present invention is useful include imaging of a beating heart, assessment the change of a physiological structure in the process of disease progression and the like.

BRIEF DESCRIPTION OF THE DRAWINGS

An embodiment of the present invention will now be described, by way of example only, with reference to the following figures, in which.

BEST MODE FOR CARRYING OUT THE INVENTION

Figure 1:
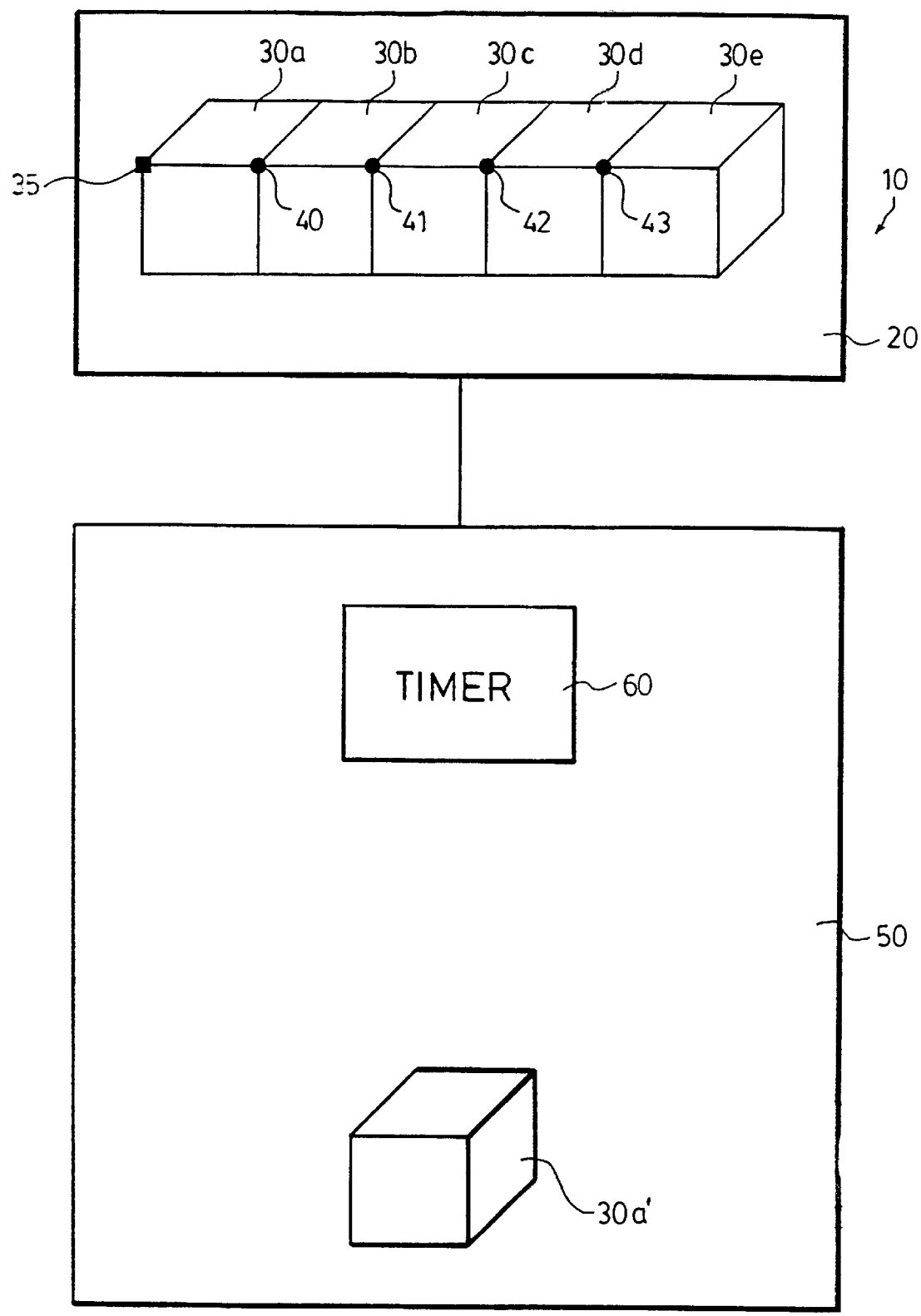
FIG. 1 is a schematic representation of the dynamic imaging method according to one embodiment of the present invention.
Figure 2A:
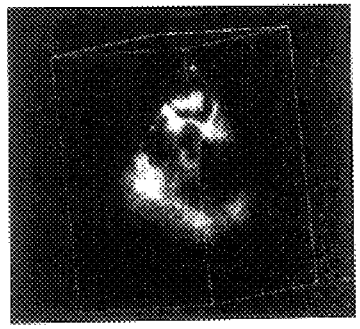
FIGS. 2a–2k illustrate time-dependent, sequential three-dimensional photographic images of a beating heart obtained using the present method and system.
Figure 2B:
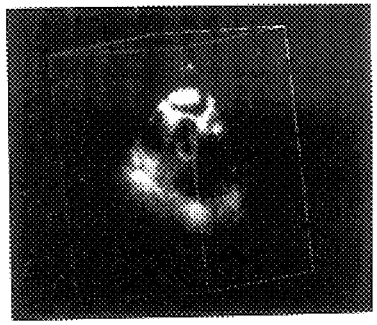
Figure 2C:
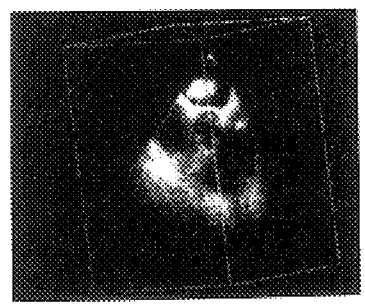
Figure 2D:
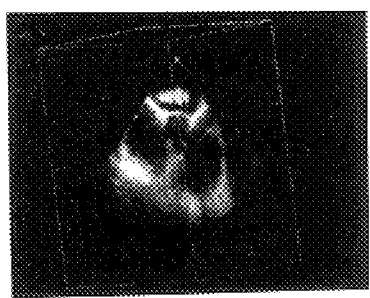
Figure 2E:
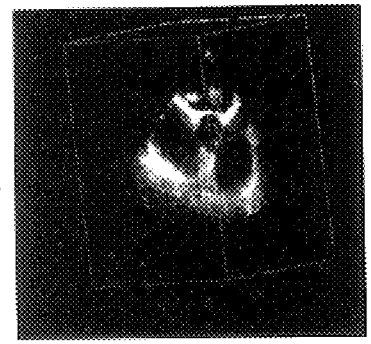
Figure 2F:
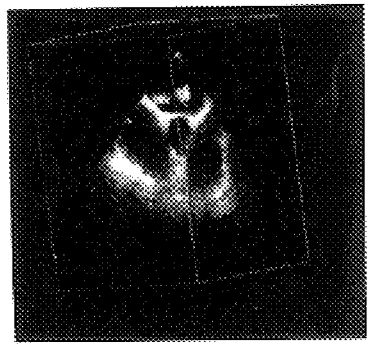
Figure 2G:
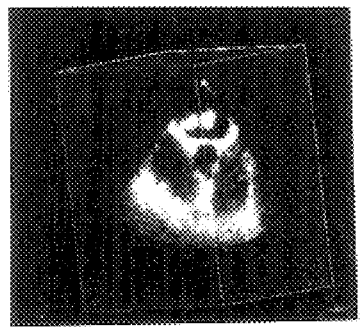
Figure 2H:
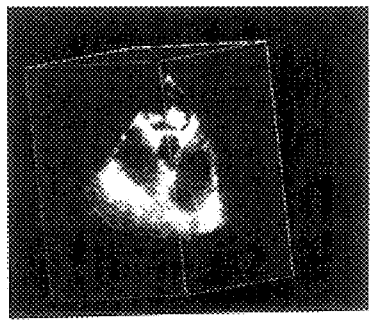
Figure 2I:
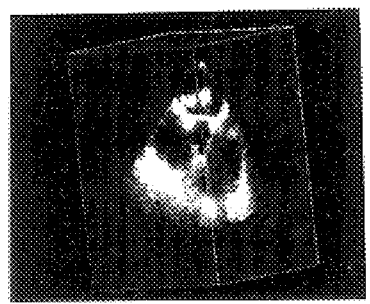
Figure 2J:
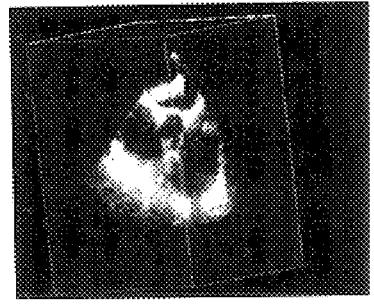
Figure 2K:
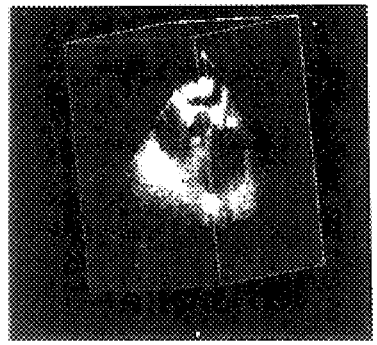

FIG. 1 illustrates the schematic for a system 10 for the dynamic display of three-dimensional (3D) images of a target. System 10 generally comprises a memory 20 to store a plurality of time-dependent 3D image data sets 30a–30e and at least one address pointer defining an independent address of a location in memory 20 of each of time-dependent 3D image data set 30a–30e. Of course those of skill in the art will recognize that the precise number of time-dependant 3D image data sets is not particularly restricted.

In the illustrated embodiment, the concordance between respective time-dependent 3D image data sets and addresses in memory 20 is as follows:

| 3D Image Data Set | Address in Memory 20 |
| --- | --- |
| 30a | 35 |
| 30b | 40 |
| 30c | 41 |
| 30d | 42 |
| 30e | 43 |

As illustrated, the individual 3D image data sets are preferably of substantially the same size and parameter.

System 10 further comprises a display means 50 which utilizes the address pointer to retrieve a first time-dependent 3D image data set 30a from address 35 in memory 20 and display the first time-dependent 3D image (30a') for a selected period of time defined by timer 60.

After the selected period of time, display means 50 retrieves another in the succession of time-dependent 3D image data sets 30b–30e from addresses 40–43, respectively, in memory 20 using the address pointer, and displays this second time-dependent 3D image, in place of the first time-dependent 3D image, for a selected period of time defined by timer 60.

As will be apparent, the duration of display of each of the successive time-dependent 3D images is not particularly limited and not all the images in a particular series need be displayed for the same length of time. Further, the number of time-dependent 3D image data sets in a series is not limited. The example in shown in FIG. 1 has a series of five time-dependent 3D image data sets. However, for the purposes of the present invention, only two different time-dependent 3D image data sets are required. Generally, there are three factors which should be taken into account in application of the present method and system: (i) the processor speed of the computer used to conduct image reconstruction; (ii) the duration of the total time interval over which the 3D image data sets are acquired; and (iii) the number of image data sets selected by the user. Thus, if the target is a beating heart and the goal is to image a single heartbeat (total time interval of approximately 1–2 seconds), given current computer processors, the number of 3D image data sets generally will be less than 20 and possibly less than 10. Alternatively, if the target is a muscle and the goal is to image it in flexure (total time interval of approximately 5 seconds), given current computer processors, the number of 3D image data sets generally will be less than about 50 and possible less than 20.

The system of the present invention is particularly useful in the field of medical imaging, where it can be used to display dynamic 3D images of moving tissue. The inventors have successfully used the system and method of this invention to produce real-time, dynamic 3D ultrasonographic images of the human heart, as will be described below.

A Hewlett-Packard HP Sonos 2500™ ECO cardiology ultrasound machine, the operation manual of which is hereby incorporated by reference, was used in standard configuration to acquire a plurality of two-dimensional (2D) ultrasound images of a beating heart. The data was acquired using an axial scanning technique with a clockwise sweep of 180°. The data acquisition time was six minutes and the data was split into twenty two successive phases of the heart beat. For ease of data management, 3D images of only eleven of these successive phases were constructed. Each 3D image comprised 91 2D frames of 224×216 pixels. This type of cardiac data acquisition and 3D image reconstruction are both well known in the art and are described in more detail in the above-mentioned U.S. Pat. No. 5,454,371 (Fenster et al.) and U.S. Pat. No. 5,562,095 (Downey et al.).

The eleven successive 3D images generated are shown in FIGS. 2a–2k. FIGS. 2a–2f show the systolic phase of the heart beat, while FIGS. 2g–2k show the diastolic phase of the heart beat.

Each of the time-dependent 3D image data sets used to generate images 2a–2k are stored in a computer memory in series to give a four-dimensional (4D) data set, where time is the fourth dimension. An address pointer defines the location within the memory of the 4D data set and the location within the memory of the start of each of the individual 3D image data sets in the 4D data set. Each image can be retrieved from memory and displayed successively for a period of time determined by the user. Further, knowing the heart-rate of the subject, the entire series of 3D images can be displayed in succession in a continuous loop to give a real-time image of the beating heart.

The present invention is not limited to the display of ultrasound images. For example, it is envisioned that this dynamic display technique may also be useful in the display of magnetic resonance or computed X-ray tomographic data. Further, it is envisioned that the 4D data set may not necessarily solely contain time-dependent 3D image data acquired using a single technique. For example, it may be desirable to show successive images of a target where each image is acquired using a different technique (i.e., combining magnetic resonance, computed X-ray tomographic and ultrasound images in a single 4D data set).

Preferably, the present method and system are directed toward ultrasonic 3D imaging. When the present method and system are used in conjunction with ultrasonic 3D imaging it is preferred to incorporate the "fast" reconstruction technique described in copending U.S. patent application Ser. No. 08/562,590 (which corresponds to International patent application publication number WO 97/20288), and U.S. provisional patent application Ser. No. 60/041,345, filed Mar. 21, 1997, the contents of each of which are hereby incorporated by reference.

When the "fast" reconstruction technique is used with the present method and system, it is preferred to design the address pointer such that it is sequentially incremented to allow it to switch between the modality described hereinabove with reference to Figure and the modality in the "fast" reconstruction technique as described in the copending applications incorporated herein by reference. The effect of this as follows. The "fast" reconstruction technique, as described in the copending applications incorporated herein by reference, allows manipulation of the displayed image via graphical input device (e.g., a mouse) to allow manipulations, with a single 3D image data set, such as rotation of the entire displayed 3D image about an arbitrary axis, translation of a selected plane of the displayed 3D image and rotation of a selected plane of the displayed 3D image about an arbitrary axis. In the context of the present method and system, the address pointer may be used to identify in a particular 3D image data set the address corresponding to a desired manipulation. Once this is done, the address pointer can be used as described hereinabove with reference to FIG. 1 to "refresh" the display image corresponding to the remaining 3D image data sets (recall it is preferred that the various 3D image data sets be of substantially the same size and parameter). The practical result of this is that the user simply manipulates one frame of the displayed image (i.e., reconstructed from one 3D image data set) and the remaining frames are displayed with a corresponding manipulation (i.e., reconstructed from each of the remaining 3D image data sets). The actual choice and design of an address pointer to switch between two modalities as described above is within the purview of a person skilled in the art.

While this invention has ben described with reference to an illustrative embodiment, this description is not intended to be construed in a limiting sense. Various modifications of the illustrated embodiment as well as other embodiments will be apparent to persons of skill in the art. For example, it is possible to modify the system to allow the user to selected the following parameters: (i) total number of 3D image data sets; (ii) time interval of which each individual 3D image data set is collected; and (iii) aggregate time interval over which all 3D image data sets are collected. Further, it is possible, and preferred, to design the system to allow the use to freeze and, optionally, manipulate (as discussed above) a single frame of the dynamic image display. It is therefore contemplated that the appended claims will cover any such modifications or embodiments.

What is claimed is:

1. A system for the dynamic display of three-dimensional (3D) images of a target, comprising:

memory means to store a plurality of time-dependent 3D image data sets;

an address pointer defining an independent address of a location in the memory means of each time-dependent 3D image data set; and display means utilizing the address pointer successively to retrieve a time-dependent 3D image data set from memory and display a time-dependent 3D image corresponding to the time-dependent 3D image data set for a selected period of time.

2. A system for the dynamic display of three-dimensional (3D) images of a target volume, the system comprising:

scanning means to scan a target volume and generate a succession of digitized two-dimensional (2D) images thereof;

timing means to determine the time interval between generation of the succession of 2D images;

reconstruction means to generate a plurality of time-dependent 3D image data sets of the target volume from the succession of digitized 2D image;

memory means to store the plurality of time-dependent 3D image data sets;

an address pointer defining an independent address of a location in the memory means of each time-dependent 3D image data set; and display means utilizing the address pointer successively to retrieve a time-dependent 3D image data set from memory and display a time-dependent 3D image corresponding to the time-dependent 3D image data set for a selected period of time.

3. A method for the dynamic display of three-dimensional (3D) images of a target, comprising the steps:
   (i) storing a plurality of time-dependent 3D image data sets in a memory;
   (ii) defining an independent address of a location in the memory means for each time-dependent 3D image data set; and
   (iii) retrieving a time-dependent 3D image data set from memory;
   (iv) displaying the time-dependent 3D image corresponding to the time-dependent 3D image data set for a selected period of time; and
   (v) repeating Steps (iii) and (iv) for each remaining time-dependent 3D image data set.

4. A method for the dynamic display of three-dimensional (3D) images of a target volume, the system comprising:
   (i) scanning a target volume and generating a succession of digitized two-dimensional (2D) images thereof;
   (ii) determining the time interval between generation of the succession of 2D images;
   (ii) generating a plurality of time-dependent 3D image data sets of the target volume from the succession of digitized 2D image;
   (iii) storing a plurality of time-dependent 3D image data sets in a memory;
   (iv) defining an independent address of a location in the memory means for each time-dependent 3D image data set; and
   (v) retrieving a time-dependent 3D image data set from memory;
   (vi) displaying the time-dependent 3D image corresponding to the time-dependent 3D image data set for a selected period of time; and
   (vii) repeating Steps (v) and (vi) for each remaining time-dependent 3D image data set.

* * * * *